(12) United States Patent
Takahashi et al.

(10) Patent No.: US 12,102,296 B2
(45) Date of Patent: Oct. 1, 2024

(54) MEDICAL IMAGING SYSTEM, MEDICAL IMAGING DEVICE, AND OPERATION METHOD

(71) Applicant: SONY GROUP CORPORATION, Tokyo (JP)

(72) Inventors: Yasuaki Takahashi, Tokyo (JP); Takeshi Miyai, Tokyo (JP); Satoshi Nagae, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/041,938

(22) PCT Filed: Aug. 18, 2021

(86) PCT No.: PCT/JP2021/030108
§ 371 (c)(1),
(2) Date: Feb. 16, 2023

(87) PCT Pub. No.: WO2022/044898
PCT Pub. Date: Mar. 3, 2022

(65) Prior Publication Data
US 2023/0397801 A1   Dec. 14, 2023

(30) Foreign Application Priority Data
Aug. 31, 2020   (JP) .................................. 2020-146084

(51) Int. Cl.
*A61B 1/045*   (2006.01)
*A61B 1/00*    (2006.01)

(52) U.S. Cl.
CPC .......... *A61B 1/045* (2013.01); *A61B 1/00009* (2013.01); *A61B 1/00186* (2013.01)

(58) Field of Classification Search
CPC ........................... A61B 1/045; A61B 1/00009
(Continued)

(56) References Cited

U.S. PATENT DOCUMENTS

2013/0041226 A1\* 2/2013 McDowall ........... H04N 13/239
600/166
2017/0351103 A1  12/2017 Duckett et al.

FOREIGN PATENT DOCUMENTS

JP   2012-169989 A   9/2012
JP   2015-091072 A   5/2015
(Continued)

OTHER PUBLICATIONS

International Search Report and Written Opinion of PCT Application No. PCT/JP2021/030108, issued on Sep. 21, 2021, 08 pages of ISRWO.

*Primary Examiner* — Jeffery A Williams
(74) *Attorney, Agent, or Firm* — CHIP LAW GROUP (57) ABSTRACT

The present disclosure relates to a medical imaging system, a medical imaging device, and an operation method that make it possible to capture a medical image in which an operative field can be better observed.

The medical imaging system includes: a first imaging element that receives light through a color filter and outputs a first image signal; a second imaging element that receives light not through a color filter and outputs a second image signal; an optical splitting system that splits incident light incident from a mount surface into light to be incident on the first imaging element and light to be incident on the second imaging element; and a signal processing unit that performs depth-of-field extension processing to generate an extended-depth-of-field image obtained by extending a depth of field using the first image signal and the second image signal. Then, the optical path length from the mount surface to the first imaging element is set to be shorter than the optical path length from the mount surface to the second imaging ele-
(Continued)

ment. The present technology can be applied to, e.g., a medical imaging system capable of capturing an EDOF image.

10 Claims, 8 Drawing Sheets

(58) Field of Classification Search
USPC .......................................................... 348/46
See application file for complete search history.

(56) References Cited

FOREIGN PATENT DOCUMENTS

| JP | 2017-158764 A | 9/2017 |
| WO | 2013/061819 A1 | 5/2013 |
| WO | 2018/186123 A1 | 10/2018 |

\* cited by examiner

MEDICAL IMAGING SYSTEM, MEDICAL IMAGING DEVICE, AND OPERATION METHOD

CROSS REFERENCE TO RELATED APPLICATIONS

This application is a U.S. National Phase of International Patent Application No. PCT/JP2021/030108 filed on Aug. 18, 2021, which claims priority benefit of Japanese Patent Application No. JP 2020-146084 filed in the Japan Patent Office on Aug. 31, 2020. Each of the above-referenced applications is hereby incorporated herein by reference in its entirety.

TECHNICAL FIELD

The present disclosure relates to a medical imaging system, a medical imaging device, and an operation method, and more particularly, to a medical imaging system, a medical imaging device, and an operation method that make it possible to capture a medical image in which an operative field can be better observed.

BACKGROUND ART

Commonly, a medical observation device such as an endoscope or a microscope acquires an image having a shallow depth of field. On the other hand, it is required to acquire a medical image having a deep depth of field, because the operative field is often deep in an operation using an endoscope, a microscope, or the like.

In view of this, an endoscope, a microscope, or the like that extends a depth of field using an extended depth of field (EDOF) optical system with a phase mask in order to increase the depth of field has been proposed as disclosed in Patent Document 1.

CITATION LIST

Patent Document

Patent Document 1: Japanese Patent Application Laid-Open No. 2017-158764

SUMMARY OF THE INVENTION

Problems to be Solved by the Invention

Meanwhile, the resolution and the depth of field are determined by the F-number of an optical system, and they have a trade-off relationship. That is, when the F-number is set to be bright and the resolution is increased, an image having a shallow depth of field is obtained, so that it is not possible to obtain image quality practically sufficient for observing the operative field. Therefore, it is required to capture a medical image which has both high resolution and deep depth of field and in which an operative field can be better observed.

The present disclosure has been made in view of the above circumstance, and is intended to make it possible to capture a medical image in which an operative field can be better observed.

Solutions to Problems

A medical imaging system and a medical imaging device according to one aspect of the present disclosure include: a first imaging element that receives light through a color filter and outputs a first image signal; a second imaging element that receives light not through a color filter and outputs a second image signal; an optical splitting system that splits incident light incident from a mount surface into light to be incident on the first imaging element and light to be incident on the second imaging element; and a signal processing unit that performs depth-of-field extension processing to generate an extended-depth-of-field image obtained by extending a depth of field using the first image signal and the second image signal, in which an optical path length from the mount surface to the first imaging element is shorter than an optical path length from the mount surface to the second imaging element.

An operation method according to one aspect of the present disclosure is an operation method for a medical imaging system, the method including: receiving light obtained by splitting incident light incident from a mount surface and outputting a first image signal by a first imaging element; receiving light split separately from the light and outputting a second image signal by a second imaging element; and performing depth-of-field extension processing to generate an extended-depth-of-field image obtained by extending a depth of field using the first image signal and the second image signal, in which the medical imaging system is configured such that an optical path length from the mount surface to the first imaging element is shorter than an optical path length from the mount surface to the second imaging element.

According to one aspect of the present disclosure, light obtained by splitting incident light incident from a mount surface is received, and a first image signal is output from the first imaging element. Further, light split separately from the light is received, and a second image signal is output from the second imaging element. Further, depth-of-field extension processing to generate an extended-depth-of-field image obtained by extending a depth of field is performed using the first image signal and the second image signal. Then, the optical path length from the mount surface to the first imaging element is set to be shorter than the optical path length from the mount surface to the second imaging element.

MODE FOR CARRYING OUT THE INVENTION

Specific embodiments to which the present technology is applied will be described below in detail with reference to the drawings.

First Configuration Example of Medical Imaging System

Figure 1:
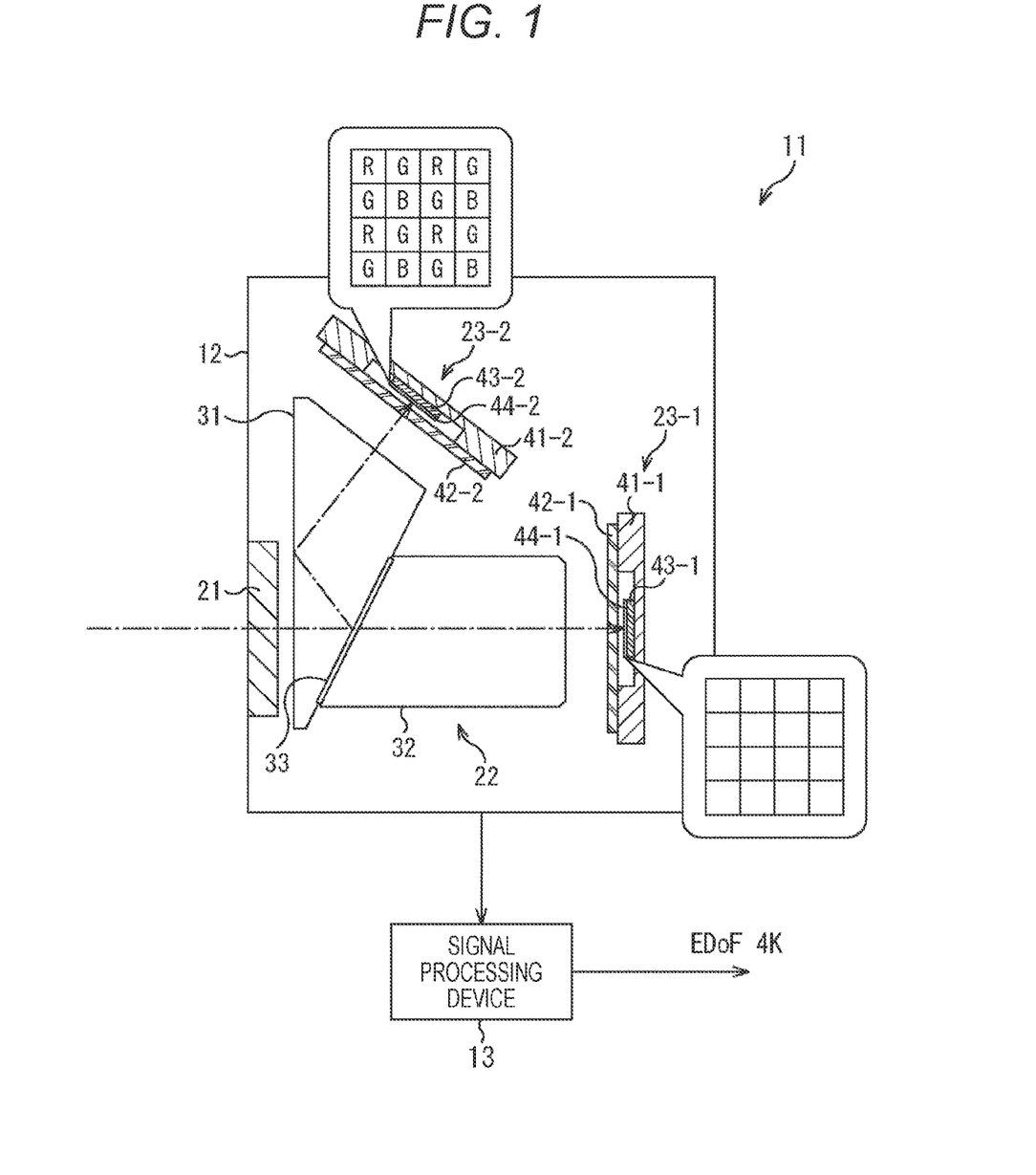
FIG. 1 is a block diagram illustrating a configuration example of a medical imaging system to which the present technology is applied according to a first embodiment.

FIG. 1 is a block diagram illustrating a configuration example of a medical imaging system to which the present technology is applied according to a first embodiment.

A medical imaging system 11 illustrated in FIG. 1 is assumed to be used for, for example, an endoscope or a surgical microscope, and includes a medical imaging device 12 and a signal processing device 13. For example, in the medical imaging system 11, light from an operative field (not illustrated) enters the medical imaging device 12 along an optical axis indicated by a dash-dot-dash line, and an image obtained by imaging the operative field is supplied from the medical imaging device 12 to the signal processing device 13. Then, an EDoF 4K image obtained as a result of performing depth-of-field extension processing in the signal processing device 13 is output from the medical imaging system 11.

The medical imaging device 12 includes a mount 21, an optical splitting system 22, and imaging modules 23-1 and 23-2.

The mount 21 is, for example, a connection portion for connecting an imaging lens having a focusing function for focusing on a certain affected part in the operative field to the medical imaging device 12.

The optical splitting system 22 splits light incident on the medical imaging device 12 via the mount 21 into light to be incident on the imaging module 23-1 and light to be incident on the imaging module 23-2.

The optical splitting system 22 includes a first prism 31, a second prism 32, and a half mirror 33. For example, in the optical splitting system 22, the half mirror 33 is disposed between the first prism 31 and the second prism 32, by which light reflected by the half mirror 33 is incident on the imaging module 23-2 through the first prism 31, and light transmitted through the half mirror 33 is incident on the imaging module 23-1 through the second prism 32.

The half mirror 33 can be set such that the reflectance and the transmittance are the same (50:50). The half mirror 33 can also be set such that the reflectance is higher than the transmittance, or the reflectance is lower than the transmittance, for example. By using the half mirror 33 in which the reflectance is set higher than the transmittance, an amount of light entering the imaging module 23-2 can be greater than an amount of light entering the imaging module 23-1. By using the half mirror 33 in which the reflectance is set lower than the transmittance, an amount of light entering the imaging module 23-1 can be greater than an amount of light entering the imaging module 23-2. Note that it is basically difficult to make the reflectance and the transmittance of the half mirror 35 variable, and therefore, the setting of the reflectance and the transmittance is a parameter adjustment item at the design stage.

The imaging module 23-1 includes an imaging element 43-1 and a filter 44-1 which are housed in a space closed by a housing 41-1 and a cover glass 42-1. In addition, the imaging module 23-2 has a similar configuration.

The filter 44-1 of the imaging module 23-1 is a transparent filter (or the filter may not be provided) that transmits light in all wavelength bands, and the imaging element 43-1 captures a luminance image (monochrome image) via the filter 44-1. A filter 44-2 of the imaging module 23-2 is an RGB filter having a Bayer array as illustrated, and an imaging element 43-2 captures a color image via the RGB filter.

In addition, the medical imaging device 12 is configured such that an optical distance from the mount 21 to the imaging module 23-2 is shorter than an optical distance from the mount 21 to the imaging module 23-1. With this configuration, when the focal length is adjusted so that the vicinity of the desired affected part is focused in the luminance image captured by the imaging module 23-1, the focal point is shifted in the image captured by the imaging module 23-2. That is, the focused position is located on a nearer point with respect to the desired affected part in the color image captured by the imaging module 23-2.

Hereinafter, a luminance image captured by the imaging module 23-1 will be referred to as a middle-luminance image, and a color image captured by the imaging module 23-2 will be referred to as a near-color image as appropriate. Therefore, in the medical imaging system 11, the middle-luminance image output from the imaging module 23-1 and the near-color image output from the imaging module 23-2 are supplied from the medical imaging device 12 to the signal processing device 13.

The signal processing device 13 performs depth-of-field extension processing to generate an EDOF image in which the depth of field is extended using the middle-luminance image and the near-color image.

First, the signal processing device 13 detects the stationarity from the middle-luminance image, and performs demosaicing (development processing) on the near-color image using the result. The signal processing device 13 performs the stationarity detection as follows. Specifically, the signal processing device 13 calculates a difference between adjacent pixels in horizontal, vertical, and oblique directions, and determines that stationarity (edge direction) appears in the direction in which the difference between the pixels is minimized. For example, in the case of a horizontal edge, the difference between pixels in the horizontal direction is the smallest. The signal processing device 13 can improve the accuracy by using the middle-luminance image having all pixels in an oblique line or the like at the point at which the performance of demosaicing is determined as compared with a case of using a green checker pattern in the Bayer array.

Next, the signal processing device 13 converts the near-color image from RGB to YCbCr and converts the middle-luminance image to Y (≈MONO). Then, the signal processing device 13 sets the image having higher contrast out of the near-color image and the middle-luminance image as Y of the image to be output. For example, the signal processing device 13 detects an edge in each of the near-color image and the middle-luminance image, and determines that the image having a larger edge has higher contrast.

Subsequently, the signal processing device 13 outputs CbCr. For example, in the case of a near-color image, each CbCr is set as CbCr to be output. On the other hand, in the case of the middle-luminance image, a process (synthesis process) of calculating a difference in contrast between the near-color image and the middle-luminance image and reducing and eliminating the calculated difference in contrast is performed on CbCr of the second signal to obtain CbCr to be output. Then, the signal processing device 13 performs unsharp processing of subtracting Y of the near-color image from Y of the middle-luminance image (Y(Middle)−Y(Near)) and adding the result to CbCr.

The signal processing device 13 can generate an EDOF image by performing the depth-of-field extension processing described above.

Note that the method for detecting stationarity from the middle-luminance image by the signal processing device 13 or parameters may be changed depending on a mode selected by the user or the surgical situation obtained by image recognition. For example, in an otolaryngological mode, the signal processing device 13 may detect stationarity based on only the center of the image, because in this mode, the inside of a thin tube is often viewed and the focal point is likely to be different between the periphery of the image and the center of the image. Furthermore, the signal processing device 13 may recognize, with image recognition, that the image includes a surgical tool such as forceps at the center, and detect the stationarity on the basis of the periphery of the distal end of the surgical tool.

In the medical imaging system 11, the middle-luminance image can be made brighter by setting the reflectance and transmittance of the half mirror 33 such that an amount of light entering the imaging module 23-1 is greater than an amount of light entering the imaging module 23-2. In the medical imaging system 11, the near-color image can be made brighter by setting the reflectance and transmittance of the half mirror 33 such that an amount of light entering the imaging module 23-2 is greater than an amount of light entering the imaging module 23-1. As described above, in the medical imaging system 11, noise can be reduced by setting the reflectance and the transmittance of the half mirror 33 according to, for example, the difference in sensitivity between the imaging modules 23-1 and 23-2.

Second Configuration Example of Medical Imaging System

Figure 2:
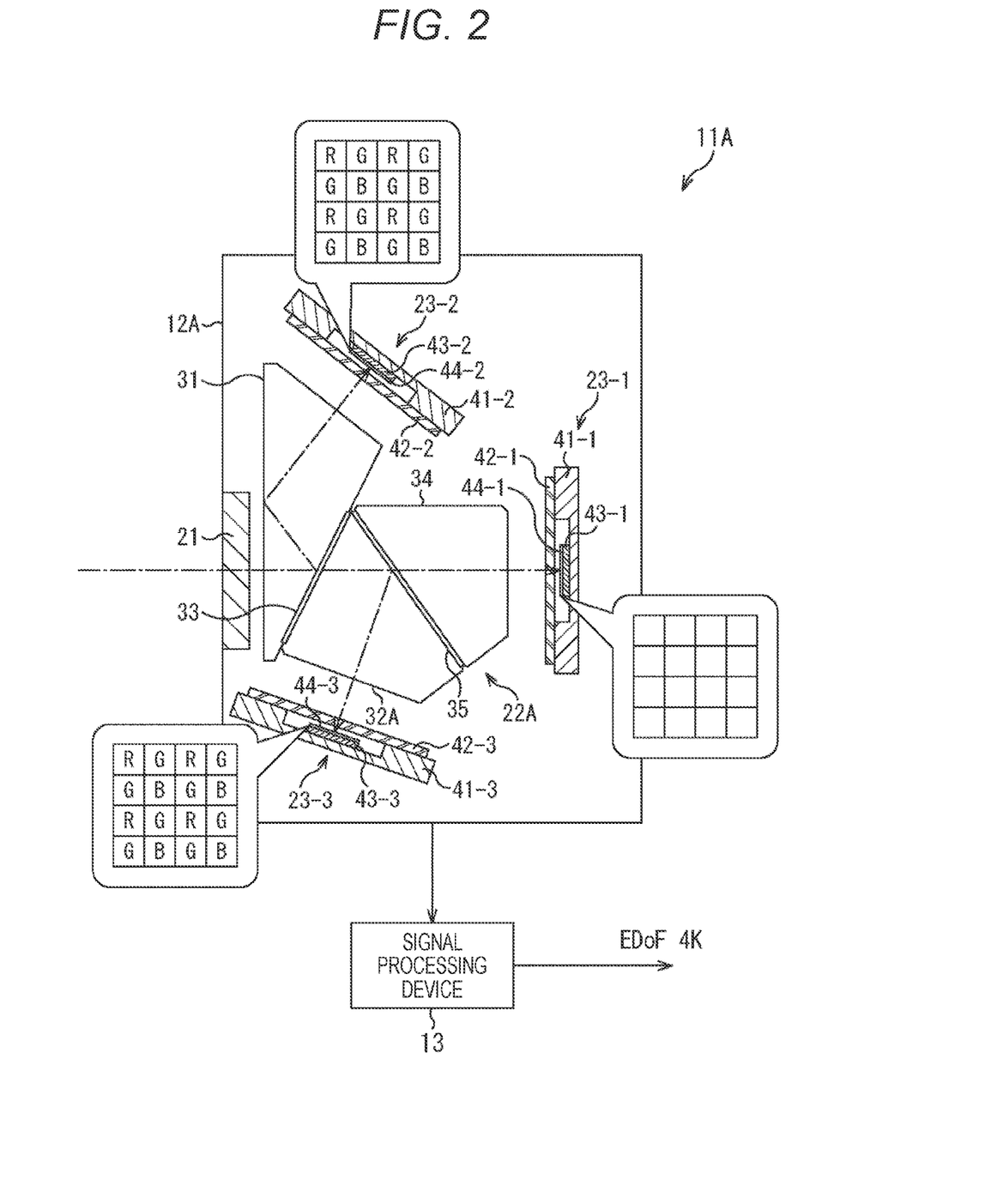
FIG. 2 is a block diagram illustrating a configuration example of a medical imaging system according to a second embodiment.

FIG. 2 is a block diagram illustrating a configuration example of a medical imaging system to which the present technology is applied according to a second embodiment. Note that, in a medical imaging system 11A illustrated in FIG. 2, components same as those in the medical imaging system 11 in FIG. 1 are identified by the same reference numerals, and the detailed description thereof will be omitted.

As illustrated in FIG. 2, the medical imaging system 11A includes a medical imaging device 12A and a signal processing device 13. The medical imaging device 12A is different from the medical imaging device 12 in FIG. 1 in that an optical splitting system 22A includes a first prism 31, a second prism 32A, a half mirror 33, a third prism 34, and a half mirror 35. That is, the optical splitting system 22A splits light incident on the medical imaging device 12 via the mount 21 in three directions.

Furthermore, the medical imaging device 12A is different from the medical imaging device 12 in FIG. 1 in including an imaging module 23-3 in addition to the imaging modules 23-1 and 23-2. Similar to the imaging module 23-2, the imaging module 23-3 can capture a color image.

In the optical splitting system 22A, the half mirror 33 is disposed between the first prism 31 and the second prism 32A so that light reflected by the half mirror 33 is incident on the imaging module 23-2 through the first prism 31. In addition, in the optical splitting system 22, the half mirror 35 is disposed between the second prism 32A and the third prism 34, by which light reflected by the half mirror 35 is incident on the imaging module 23-3 through the second prism 32, and light transmitted through the half mirror 35 is incident on the imaging module 23-1 through the third prism 34.

Similar to the medical imaging device 12 in FIG. 1, the medical imaging device 12A can set the reflectance and the transmittance of the half mirrors 33 and 35 according to a difference in sensitivity between the imaging modules 23-1 to 23-3.

In addition, the medical imaging device 12A is configured such that an optical distance from the mount 21 to the imaging module 23-3 is longer than an optical distance from the mount 21 to the imaging module 23-1. With this configuration, when the focal length is adjusted so that the vicinity of the desired affected part is focused in the luminance image captured by the imaging module 23-1, the focal point is shifted in the image captured by the imaging module 23-3. That is, the focused position is located on a point farther from the desired affected part in the color image captured by the imaging module 23-3.

Hereinafter, the color image captured by the imaging module 23-3 is appropriately referred to as a far-color image. Therefore, in the medical imaging system 11A, the middle-luminance image output from the imaging module 23-1, the near-color image output from the imaging module 23-2, and the far-color image output from the imaging module 23-3 are supplied from the medical imaging device 12A to the signal processing device 13.

The signal processing device 13 performs depth-of-field extension processing to generate an EDOF image in which the depth of field is extended using the middle-luminance image, the near-color image, and the far-color image, as in the signal processing device 13 in FIG. 1.

Note that the medical imaging device 12A may include four imaging modules 23 by adding an IR imaging module (image sensor for long-wavelength light source). In this configuration, the IR imaging module is preferably disposed between the imaging module 23-1 for a middle-luminance image and the imaging module 23-3 for a far-color image. In addition, the medical imaging device 12A may include four imaging modules 23 by adding a V imaging module (image sensor for short-wavelength light source). In this configuration, the V imaging module is preferably disposed between the imaging module 23-1 for a middle-luminance image and the imaging module 23-2 for a near-color image.

In addition, the medical imaging device 12A preferably has a relationship of (B−C)>(C−A) between a distance A from the mount surface to the imaging module 23-2 for a near-color image, a distance B from the mount surface to the imaging module 23-1 for a middle-luminance image, and a distance C from the mount surface to the imaging module 23-3 for a far-color image. That is, this relationship indicates that the imaging module 23-1 for a middle-luminance image is disposed on the far side with respect to the center between the imaging module 23-2 for a near-color image and the imaging module 23-3 for a far-color image. This is because a far-color image is important in most cases.

Third Configuration Example of Medical Imaging System

Figure 3:
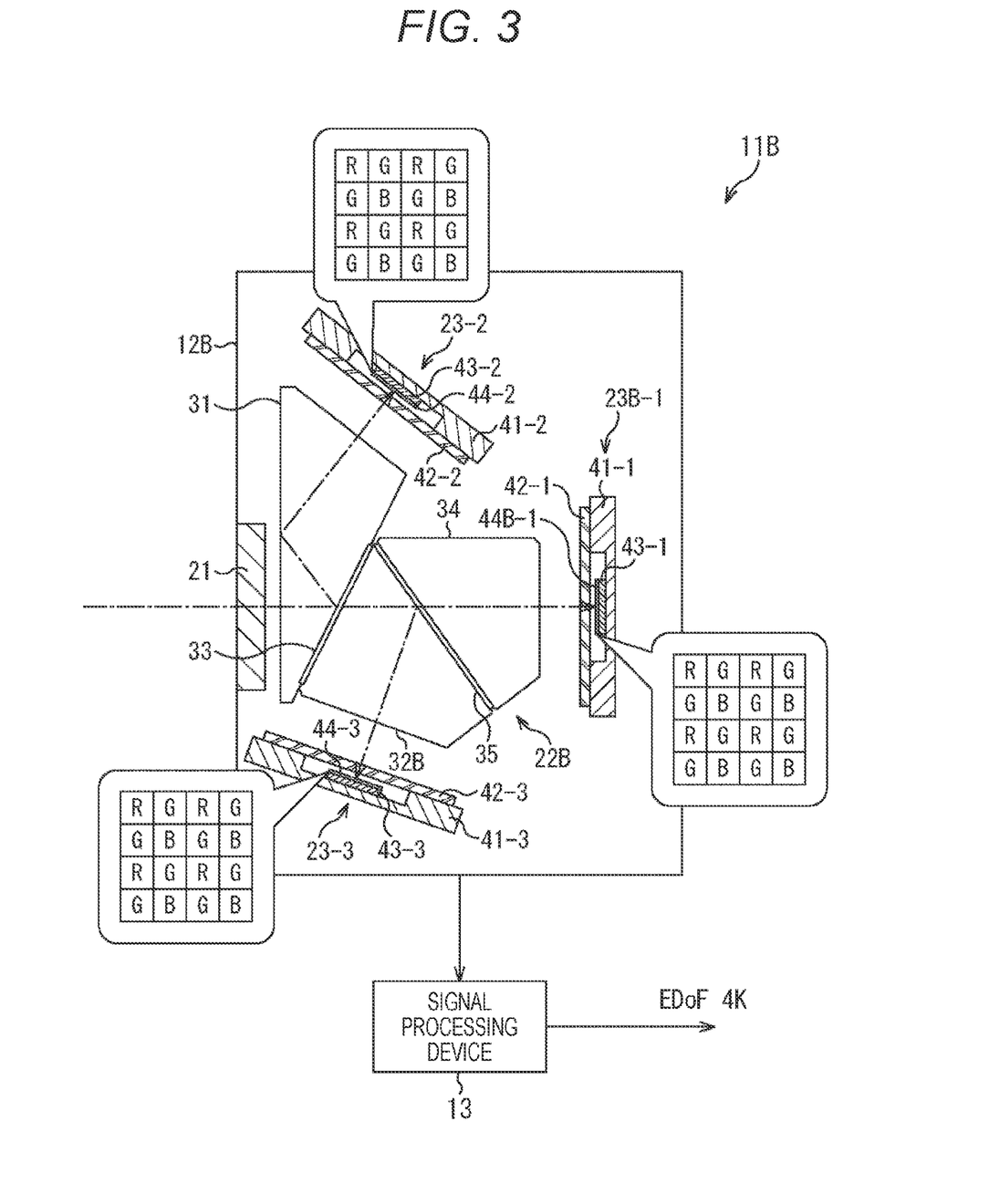
FIG. 3 is a block diagram illustrating a configuration example of a medical imaging system according to a third embodiment.

FIG. 3 is a block diagram illustrating a configuration example of a medical imaging system to which the present technology is applied according to a third embodiment. Note that, in a medical imaging system 11B illustrated in FIG. 3, components same as those in the medical imaging system 11 in FIG. 1 are identified by the same reference numerals, and the detailed description thereof will be omitted.

As illustrated in FIG. 3, the medical imaging system 11B includes a medical imaging device 12B and a signal processing device 13. The medical imaging device 12B is different from the medical imaging device 12 in FIG. 1 in that an optical splitting system 22 includes a first prism 31, a second prism 32B, a half mirror 33, a third prism 34, and a half mirror 35. That is, the optical splitting system 22B splits light incident on the medical imaging device 12 via the mount 21 in three directions as in the optical splitting system 22A in FIG. 2.

Furthermore, the medical imaging device 12B is different from the medical imaging device 12 in FIG. 1 in including an imaging module 23-3 in addition to the imaging modules 23B-1 and 23-2. Similar to the imaging module 23-2, the imaging module 23-3 can capture a color image. Then, the imaging module 23B-1 is different from the imaging module 23-1 in FIG. 1 in that a filter 44B-1 of the imaging module 23B-1 is an RGB filter having a Bayer array as illustrated, and an imaging element 43-1 captures a color image through the filter 44B-1.

In addition, the medical imaging device 12B is configured such that an optical distance from the mount 21 to the imaging module 23-3 is longer than an optical distance from the mount 21 to the imaging module 23B-1. With this configuration, when the focal length is adjusted so that the vicinity of the desired affected part is focused in the color image captured by the imaging module 23B-1, the focal point is shifted in the image captured by the imaging module 23-3. That is, the focused position is located on a point farther from the desired affected part in the color image captured by the imaging module 23-3.

Hereinafter, the color image captured by the imaging module 23B-1 will be referred to as a middle-color image, and the color image captured by the imaging module 23-3 will be referred to as a far-color image as appropriate. Therefore, in the medical imaging system 11, the middle-color image output from the imaging module 23B-1, the near-color image output from the imaging module 23-2, and the far-color image output from the imaging module 23-3 are supplied from the imaging module 23-2 to the signal processing device 13.

Furthermore, in the medical imaging device 12B, the imaging module 23-3 for a far-color image and the imaging module 23-2 for a near-color image are arranged to be shifted by one pixel in a direction of a horizontal plane (vertical direction or horizontal direction) orthogonal to the optical axis with respect to the imaging module 23B-1 for a middle-color image.

The signal processing device 13 performs depth-of-field extension processing to generate an EDOF image in which the depth of field is extended using the middle-color image, the near-color image, and the far-color image.

First, the signal processing device 13 uses green (Gr, Gb) in the Bayer array in the middle-color image, the near-color image, and the far-color image to select an image with the highest contrast and an image with the second highest contrast. The two images selected here are either a combination of the near-color image and the middle-color image or a combination of the middle-color image and the far-color image.

Next, the signal processing device 13 detects stationarity using not a checker pattern but images of all pixels including green pixel values by combining green (Gr, Gb) in the Bayer array of the two selected images.

Then, the signal processing device 13 performs demosaicing on the image having the highest contrast using the result of the stationarity detection, and then generates and outputs RGB.

In the medical imaging system 11B, the reflectance and the transmittance of the half mirror 33 are preferably set so that an amount of light incident on the imaging module 23B-1 for a middle-color image increases due to the middle-color image being always selected.

Figure 4:
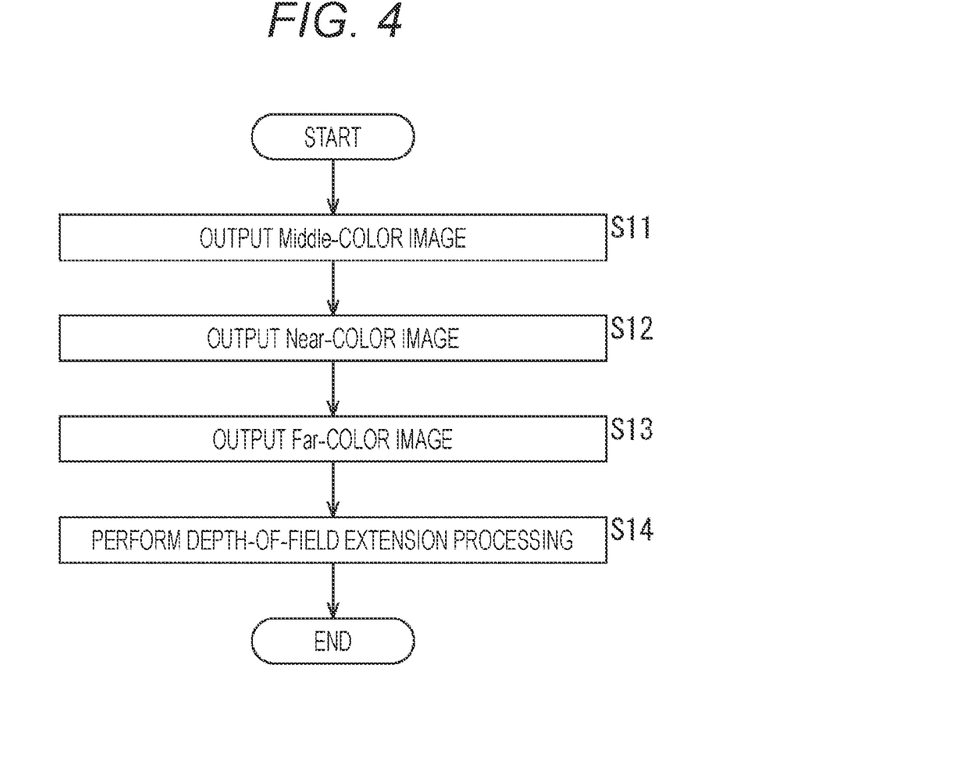
FIG. 4 is a flowchart for describing a method for capturing a medical image.

A method for capturing a medical image by the medical imaging system 11B will be described with reference to a flowchart of FIG. 4.

In step S11, the imaging module 23B-1 acquires the middle-color image and outputs the same to the signal processing device 13.

In step S12, the imaging module 23-2 acquires the near-color image and outputs the same to the signal processing device 13.

In step S13, the imaging module 23-3 acquires the far-color image and outputs the same to the signal processing device 13.

In step S14, the signal processing device 13 performs depth-of-field extension processing to generate an EDOF image in which the depth of field is extended using the middle-color image, the near-color image, and the far-color image, and outputs the generated EDOF image.

As described above, the medical imaging system 11 according to each of the above-described embodiments can simultaneously acquire three images having different focuses which are a middle-luminance image (middle-color image), a near-color image, and a far-color image. From these three images, the medical imaging system 11 can generate an image with high resolution and a depth of field, and satisfactory observation is possible with the generated image.

Note that, for example, Japanese Patent Application Laid-Open No. 2012-169989 discloses a technique of obtaining a good interpolation image without a false color by using a luminance signal of a monochrome imaging element when demosaicing is performed on a signal obtained from an RGB imaging element of a Bayer array, but does not disclose extension of a depth of field. On the other hand, the medical imaging system 11 can acquire a high-resolution image and an image with an extended depth of field.

Configuration Example of Electronic Apparatus

The above-described medical imaging device 12 is applicable to various electronic apparatuses including an imaging system such as a digital still camera and a digital video camera, a mobile phone having an imaging function, and another device having an imaging function.

Figure 5:
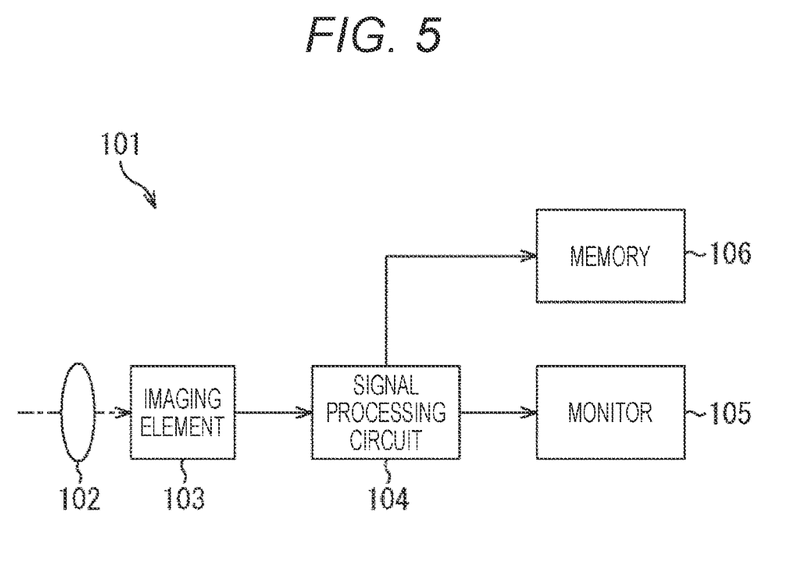
FIG. 5 is a block diagram illustrating a configuration example of an imaging device.

FIG. 5 is a block diagram illustrating a configuration example of an imaging device mounted on an electronic apparatus.

As illustrated in FIG. 5, an imaging device 101 includes an optical system 102, an imaging element 103, a signal processing circuit 104, a monitor 105, and a memory 106, and can capture a still image and a moving image.

The optical system 102 includes one or a plurality of lenses, guides image light (incident light) from a subject to the imaging element 103, and forms an image on a light receiving surface (sensor unit) of the imaging element 103.

As the imaging element 103, the medical imaging device 12 described above is applied. Electrons are accumulated in the imaging element 103 for a certain period according to an image formed on the light receiving surface via the optical system 102. Then, a signal corresponding to the electrons accumulated in the imaging element 103 is supplied to the signal processing circuit 104.

The signal processing circuit 104 performs various types of signal processing on the pixel signal output from the imaging element 103. An image (image data) obtained by performing signal processing by the signal processing circuit 104 is supplied to and displayed on the monitor 105, or supplied to and stored (recorded) in the memory 106.

The imaging device 101 configured as described above can capture, for example, a medical image in which the operative field can be better observed by applying the above-described medical imaging device 12.

Use Example of Image Sensor

Figure 6:
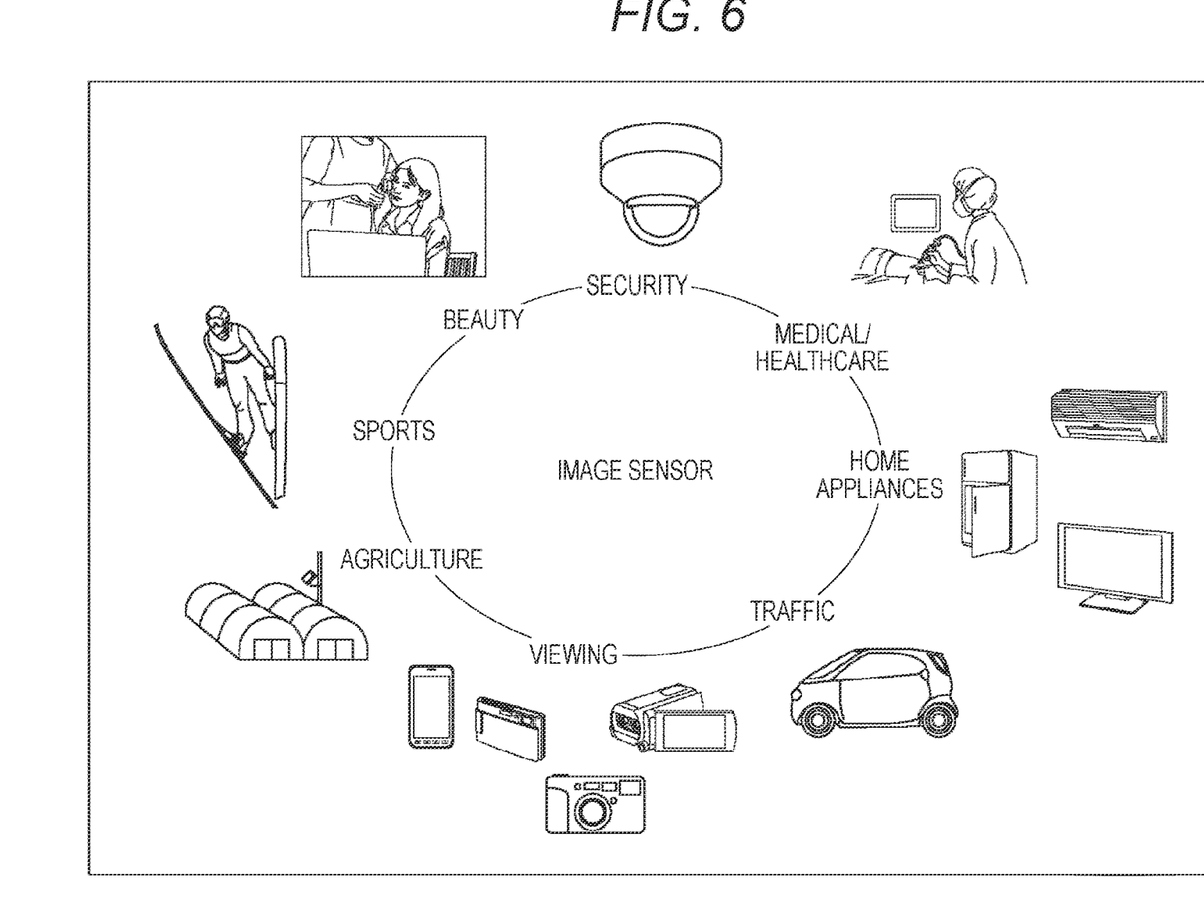
FIG. 6 is a diagram illustrating a use example of an image sensor.

FIG. 6 is a diagram illustrating a use example of the above-mentioned image sensor (imaging element).

The image sensor can be used in various cases for sensing light such as visible light, infrared light, ultraviolet light, and X-ray as described below, for example.

- Devices that capture images used for viewing, such as digital cameras and mobile devices with camera functions
- Devices used for traffic such as: in-vehicle sensors that capture an image of an environment in front of, at the rear of, and around automobile, the interior of the automobile, etc. for safe driving such as automatic stop, recognition of the condition of driver, etc.; surveillance cameras that monitor traveling vehicles or road; or distance measurement sensors that measure the distance between vehicles, etc.
- Devices used in home appliances such as TVs, refrigerators, and air conditioners to capture an image of user's gesture and perform operations according to the gesture
- Devices used for medical and healthcare, such as endoscopes and devices that perform angiography by receiving infrared light
- Devices used for security, such as surveillance cameras for crime prevention and cameras for personal authentication
- Devices used for beauty, such as skin measuring devices that capture an image of the skin and microscopes that capture the image of the scalp
- Devices used for sports such as action cameras and wearable cameras for sporting use, etc.
- Devices used for agriculture, such as cameras for monitoring the condition of fields and crops Application Example The technology according to the present disclosure can be applied to a medical imaging system. The medical imaging system is a medical system using an imaging technology, and is, for example, an endoscope system or a microscope system.

Endoscope System

Figure 7:
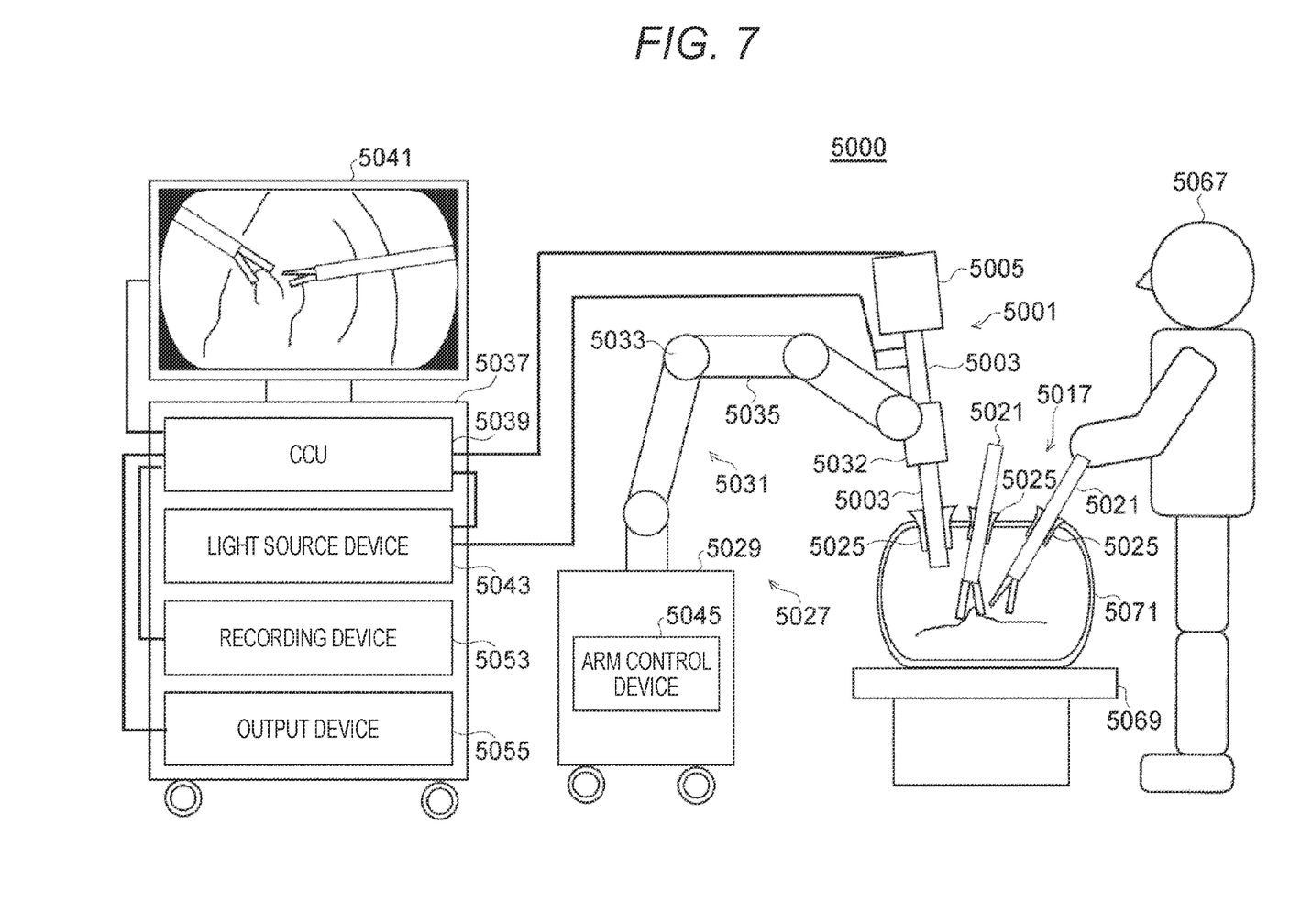
FIG. 7 is a diagram illustrating an example of a schematic configuration of an endoscope system.
Figure 8:
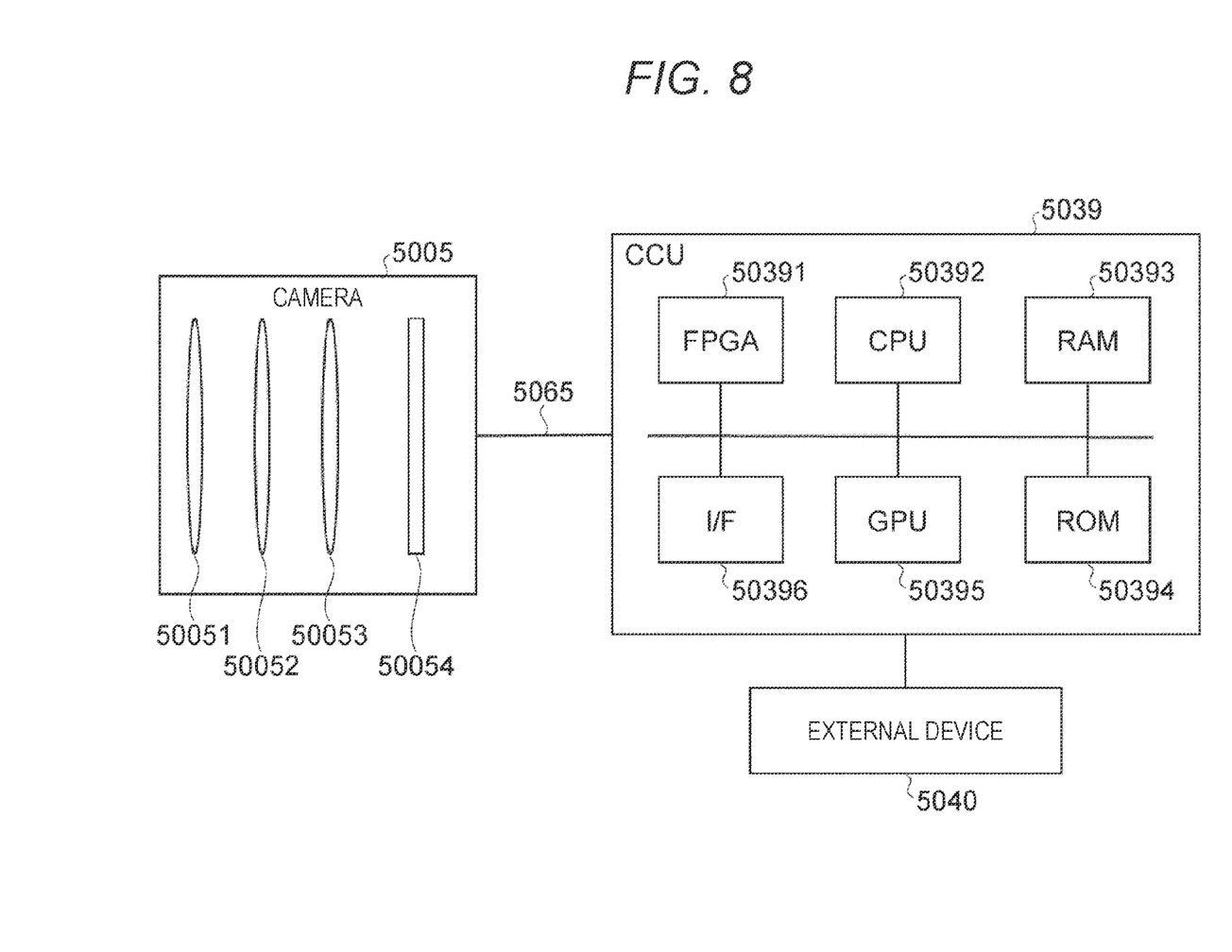
FIG. 8 is a block diagram illustrating an example of a functional configuration of a camera head and a camera control unit (CCU) illustrated in FIG. 7.

An example of the endoscope system will be described with reference to FIGS. 7 and 8. FIG. 7 is a diagram illustrating an example of a schematic configuration of an endoscope system 5000 to which the technology according to the present disclosure is applicable. FIG. 8 is a diagram illustrating an example of a configuration of an endoscope 5001 and a camera control unit (CCU) 5039. FIG. 7 illustrates a situation where an operator (for example, a doctor) 5067 who is a participant of an operation performs the operation on a patient 5071 on a patient bed 5069 using the endoscope system 5000. As illustrated in FIG. 7, the endoscope system 5000 includes the endoscope 5001 that is a medical imaging device, the CCU 5039, a light source device 5043, a recording device 5053, an output device 5055, and a support device 5027 for supporting the endoscope 5001.

In endoscopic surgery, insertion assisting tools called trocars 5025 are punctured into the patient 5071. Then, a scope 5003 connected to the endoscope 5001 and surgical tools 5021 are inserted into a body of the patient 5071 through the trocars 5025. The surgical tools 5021 include: an energy device such as an electric scalpel; and forceps, for example.

A surgical image that is a medical image in which the inside of the body of the patient 5071 is captured by the endoscope 5001 is displayed on a display device 5041. The operator 5067 performs a procedure on a surgical target using the surgical tools 5021 while viewing the surgical image displayed on the display device 5041. The medical image is not limited to the surgical image, and may be a diagnostic image captured during diagnosis.

Endoscope

The endoscope 5001 is a camera for capturing the inside of the body of the patient 5071, and is, for example, a camera head including a condensing optical system 50051 for condensing incident light, a zooming optical system 50052 capable of optical zooming by changing a focal length of the camera, a focusing optical system 50053 capable of focus adjustment by changing the focal length of the camera, and a light receiving sensor 50054 as illustrated in FIG. 8. The endoscope 5001 condenses the light through the connected scope 5003 on the light receiving sensor 50054 to generate a pixel signal, and outputs the pixel signal through a transmission system to the CCU 5039. The scope 5003 is an insertion part that includes an objective lens at a distal end and guides the light from the connected light source device 5043 into the body of the patient 5071. The scope 5003 is, for example, a rigid scope for a rigid endoscope and a flexible scope for a flexible endoscope. The pixel signal only needs to be a signal based on a signal output from a pixel, and is, for example, a raw signal or an image signal. The transmission system connecting the endoscope 5001 to the CCU 5039 may include a memory, and the memory may store parameters related to the endoscope 5001 and the CCU 5039. The memory may be disposed at a connection portion of the transmission system or on a cable. For example, the memory of the transmission system may store the parameters before shipment of the endoscope 5001 or the parameters changed when current is applied, and an operation of the endoscope may be changed based on the parameters read from the memory. A set of the camera and the transmission system may be referred to as an endoscope. The light receiving sensor 50054 is a sensor for converting the received light into the pixel signal, and is, for example, a complementary metal-oxide-semiconductor (CMOS) imaging sensor. The light receiving sensor 50054 is preferably an imaging sensor having a Bayer array capable of color imaging. The light receiving sensor 50054 is also preferably an imaging sensor having a number of pixels corresponding to a resolution of, for example, 4K (3840 horizontal pixels× 2160 vertical pixels), 8K (7680 horizontal pixels×4320 vertical pixels), or square 4K (3840 or more horizontal pixels×3840 or more vertical pixels). The light receiving sensor 50054 may be one sensor chip, or a plurality of sensor chips. For example, a prism may be provided to separate the incident light into predetermined wavelength bands, and the wavelength bands may be imaged by different light receiving sensors. A plurality of light receiving sensors may be provided for stereoscopic viewing. The light receiving sensor 50054 may be a sensor having a chip structure including an arithmetic processing circuit for image processing, or may be a sensor for time of flight (ToF). The transmission system is, for example, an optical fiber cable system or a wireless transmission system. The wireless transmission only needs to be capable of transmitting the pixel signal generated by the endoscope 5001, and, for example, the endoscope 5001 may be wirelessly connected to the CCU 5039, or the endoscope 5001 may be connected to the CCU 5039 via a base station in an operating room. At this time, the endoscope 5001 may transmit not only the pixel signal, but also simultaneously information (for example, a processing priority of the pixel signal and/or a synchronization signal) related to the pixel signal. In the endoscope, the scope may be integrated with the camera head, and the light receiving sensor may be provided at the distal end of the scope.

CCU (Camera Control Unit)

The CCU 5039 is a control device for controlling the endoscope 5001 and the light source device 5043 connected to the CCU 5039 in an integrated manner, and is, for example, as illustrated in FIG. 8, an image processing device including a field-programmable gate array (FPGA) 50391, a central processing unit (CPU) 50392, a random access memory (RAM) 50393, a read-only memory (ROM) 50394, a graphics processing unit (GPU) 50395, and an interface (I/F) 50396. The CCU 5039 may control the display device 5041, the recording device 5053, and the output device 5055 connected to the CCU 5039 in an integrated manner. The CCU 5039 controls, for example, irradiation timing, irradiation intensity, and a type of an irradiation light source of the light source device 5043. The CCU 5039 also performs image processing, such as development processing (for example, demosaic processing) and correction processing, on the pixel signal output from the endoscope 5001, and outputs the processed image signal (for example, an image) to an external device such as the display device 5041. The CCU 5039 also transmits a control signal to the endoscope 5001 to control driving of the endoscope 5001. The control signal is information regarding an imaging condition such as a magnification or the focal length of the camera. The CCU 5039 may have a function to down-convert the image, and may be configured to be capable of simultaneously outputting a higher-resolution (for example, 4K) image to the display device 5041 and a lower-resolution (for example, high-definition (HD)) image to the recording device 5053.

In addition, the CCU 5039 may be connected to external equipment via an IP converter for converting the signal into a predetermined communication protocol (such as the Internet Protocol (IP)). The connection between the IP converter and the external equipment may be established using a wired network, or a part or the whole of the network may be established using a wireless network. For example, the IP converter on the CCU 5039 side may have a wireless communication function, and may transmit the received image to an IP switcher or an output side IP converter via a wireless communication network, such as the fifth-generation mobile communication system (5G) or the sixth-generation mobile communication system (6G).

Light Source Device

The light source device 5043 is a device capable of emitting the light having predetermined wavelength bands, and includes, for example, a plurality of light sources and a light source optical system for guiding the light of the light sources. The light sources are, for example, xenon lamps, light-emitting diode (LED) light sources, or laser diode (LD) light sources. The light source device 5043 includes, for example, the LED light sources corresponding to three respective primary colors of red (R), green (G), and blue (B), and controls output intensity and output timing of each of the light sources to emit white light. The light source device 5043 may include a light source capable of emitting special light used for special light observation, in addition to the light sources for emitting normal light for normal light observation. The special light is light having a predetermined wavelength band different from that of the normal light being light for the normal light observation, and is, for example, near-infrared light (light having a wavelength of 760 nm or longer), infrared light, blue light, or ultraviolet light. The normal light is, for example, the white light or green light. In narrow band imaging that is a kind of special light observation, blue light and green light are alternately emitted, and thus the narrow band imaging can image a predetermined tissue such as a blood vessel in a mucosal surface at high contrast using wavelength dependence of light absorption in the tissue of the body. In fluorescence observation that is a kind of special light observation, excitation light is emitted for exciting a reagent injected into the tissue of the body, and fluorescence emitted by the tissue of the body or the reagent is received to obtain a fluorescent image, and thus the fluorescence observation can facilitate the operator to view, for example, the tissue of the body that is difficult to be viewed by the operator with the normal light. For example, in fluorescence observation using infrared light, near infrared light is emitted as excitation light to excite a reagent, such as indocyanine green (ICG), injected into the tissue of the body, whereby the fluorescence observation can facilitate viewing of a deep structure of the tissue of the body. In addition, in the fluorescence observation, a reagent (such as PDD or 5-aminolevulinic acid (5-ALA)) may be used that emits fluorescence in a red wavelength band by being excited by the special light in a blue wavelength band. The type of the irradiation light of the light source device 5043 is set by control of the CCU 5039. The CCU 5039 may have a mode of controlling the light source device 5043 and the endoscope 5001 to alternately perform the normal light observation and the special light observation. At this time, information based on a pixel signal obtained by the special light observation is preferably superimposed on a pixel signal obtained by the normal light observation.

Recording Device

The recording device 5053 is a device for recording the pixel acquired from the CCU 5039, and is, for example, a recorder. The recording device 5053 records an image acquired from the CCU 5039 in a hard disk drive (HDD), a Super Density Disc (SDD), and/or an optical disc. The recording device 5053 may be connected to a network in a hospital to be accessible from equipment outside the operating room. The recording device 5053 may have a down-convert function or an up-convert function.

Display Device

The display device 5041 is a device capable of displaying the image, and is, for example, a display monitor. The display device 5041 displays the display image based on the pixel signal which has been subjected to the image processing by the CCU 5039 under the control of the CCU 5039. The display device 5041 may include a camera and a microphone to function as an input device that allows instruction input through gaze recognition, voice recognition, and gesture.

Output Device

The output device 5055 is a device for outputting the information acquired from the CCU 5039, and is, for example, a printer. The output device 5055 prints, for example, a print image based on the pixel signal acquired from the CCU 5039 on a sheet of paper.

Support Device

The support device 5027 is an articulated arm including a base 5029 including an arm control device 5045, an arm 5031 extending from the base 5029, and a holding part 5032 mounted at a distal end of the arm 5031. The arm control device 5045 includes a processor such as a CPU, and operates according to a predetermined computer program to control driving of the arm 5031. The support device 5027 uses the arm control device 5045 to control parameters including, for example, lengths of links 5035 constituting the arm 5031 and rotation angles and torque of joints 5033 so as to control, for example, the position and attitude of the endoscope 5001 held by the holding part 5032. This control can change the position or attitude of the endoscope 5001 to a desired position or attitude, makes it possible to insert the scope 5003 into the patient 5071, and can change the observed area in the body. The support device 5027 functions as an endoscope support arm for supporting the endoscope 5001 during the operation. Thus, the support device 5027 can play a role of a scopist who is an assistant holding the endoscope 5001. The support device 5027 may be a device for holding a microscope device 5301 to be described later, and can be called a medical support arm. The support device 5027 may be controlled using an autonomous control method by the arm control device 5045, or may be controlled using a control method in which the arm control device 5045 performs the control based on input of a user. The control method may be, for example, a master-slave method in which the support device 5027 serving as a slave device is controlled on the basis of a movement of a master device at a hand of the user. The support device 5027 may be remotely controllable from outside the operating room.

The example of the endoscope system 5000 to which the technology according to the present disclosure is applicable has been described above. For example, the technology according to the present disclosure may be applied to a microscope system.

Microscope System

Figure 9:
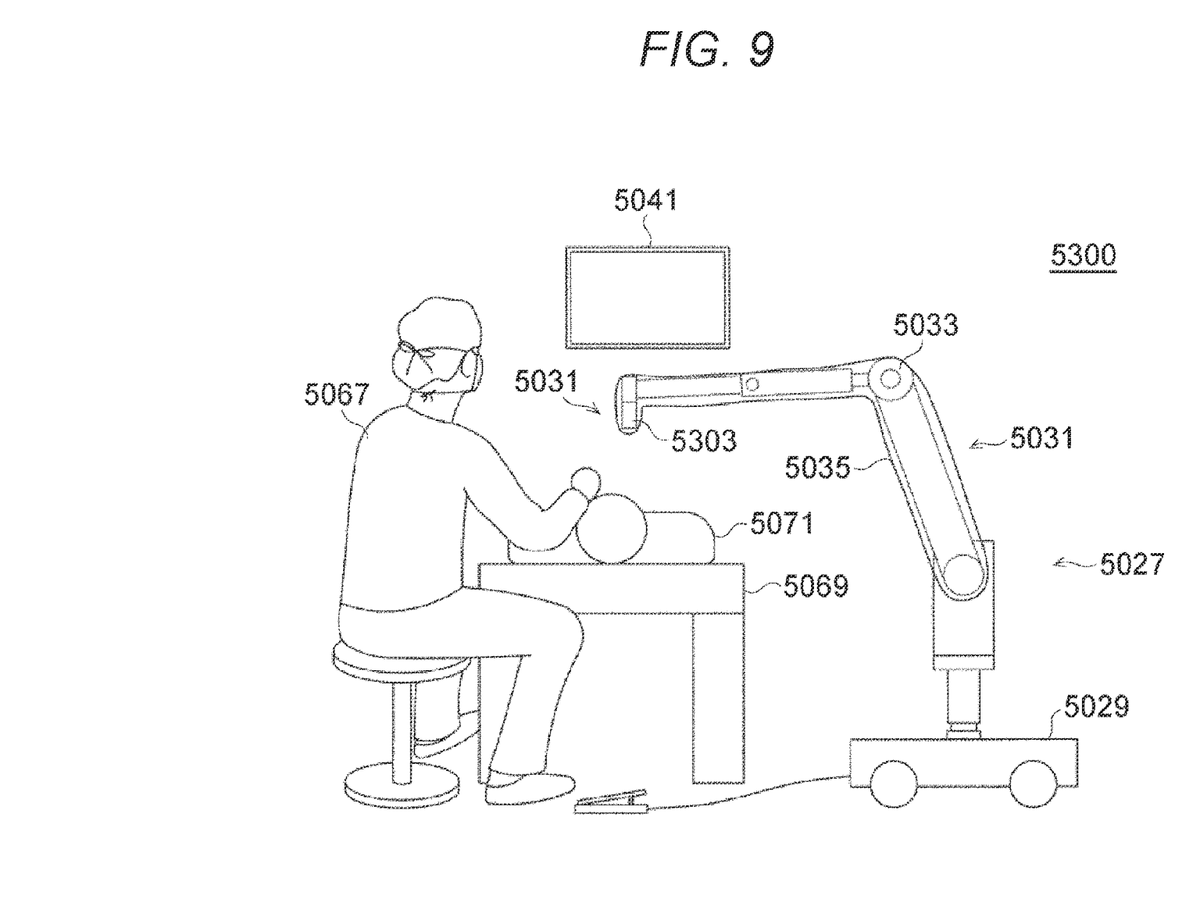
FIG. 9 is a diagram illustrating an example of a schematic configuration of a microscopic surgery system.

FIG. 9 is a diagram illustrating an example of a schematic configuration of a microscopic surgery system to which the technology according to the present disclosure is applicable. In the following description, the same components as those of the endoscope system 5000 will be denoted by the same reference numerals, and the description thereof will not be repeated.

FIG. 9 schematically illustrates a situation where the operator 5067 performs an operation on the patient 5071 on the patient bed 5069 using a microscopic surgery system 5300. For the sake of simplicity, FIG. 9 does not illustrate a cart 5037 among the components of the microscopic surgery system 5300, and illustrates the microscope device 5301 instead of the endoscope 5001 in a simplified manner. The microscope device 5301 may refer to a microscope 5303 provided at the distal end of the links 5035, or may refer to the overall configuration including the microscope 5303 and the support device 5027.

As illustrated in FIG. 9, during the operation, the microscopic surgery system 5300 is used to display an image of a surgical site captured by the microscope device 5301 in a magnified manner on the display device 5041 installed in the operating room. The display device 5041 is installed in a position facing the operator 5067, and the operator 5067 performs various procedures, such as excision of an affected part, on the surgical site while observing the state of the surgical site using the image displayed on the display device 5041.

The respective examples of the endoscope system 5000 and the microscopic surgery system 5300 to which the technology according to the present disclosure is applicable have been described above. Systems to which the technology according to the present disclosure is applicable are not limited to such examples. For example, the support device 5027 can support, at the distal end thereof, another observation device or another surgical tool instead of the endoscope 5001 or the microscope 5303. Examples of the other applicable observation device include forceps, tweezers, a pneumoperitoneum tube for pneumoperitoneum, and an energy treatment tool for incising a tissue or sealing a blood vessel by cauterization. By using the support device to support the observation device or the surgical tool described above, the position thereof can be more stably fixed and the load of the medical staff can be lower than in a case where the medical staff manually supports the observation device or the surgical tool. The technology according to the present disclosure may be applied to a support device for supporting such a component other than the microscope.

The technology according to the present disclosure may be applied to the endoscope 5001 or the microscope device 5301 in the configuration described above. Thus, it is possible to capture a medical image in which the operative field can be better observed, and it is possible to perform the operation more safely and more reliably.

Example of Combination of Configurations

It is to be noted that the present technology may also have the following configurations.

(1)

A medical imaging system including:

a first imaging element that receives light through a color filter and outputs a first image signal;

a second imaging element that receives light not through a color filter and outputs a second image signal;

an optical splitting system that splits incident light incident from a mount surface into light to be incident on the first imaging element and light to be incident on the second imaging element; and a signal processing unit that performs depth-of-field extension processing to generate an extended-depth-of-field image obtained by extending a depth of field using the first image signal and the second image signal, in which an optical path length from the mount surface to the first imaging element is shorter than an optical path length from the mount surface to the second imaging element.

(2)

The medical imaging system according to (1), in which the optical splitting system includes an optical element that reflects a part of light and transmits a part of light, and the optical element has a transmittance set according to a difference in sensitivity between the first imaging element and the second imaging element.

(3)

The medical imaging system according to (1) or (2), in which
the signal processing unit performs stationarity detection on the second image signal and performs development processing on the first image signal using a result of the stationarity detection.

(4)

The medical imaging system according to (3), in which
the signal processing unit acquires a difference between adjacent pixels in at least one of a horizontal direction, a vertical direction, or an oblique direction, and performs the stationarity detection assuming that stationarity appears in a direction in which the difference between the pixels is minimized.

(5)

The medical imaging system according to (3), in which
the signal processing unit calculates a difference in contrast between the first image signal and the second image signal and performs processing to reduce the difference in contrast.

(6)

The medical imaging system according to (3), in which
the signal processing unit changes a parameter and a method of the stationarity detection on the basis of a mode selected by a user or a surgical situation obtained by image recognition.

(7)

The medical imaging system according to any one of (1) to (6), further including
a third imaging element that receives light through a color filter and outputs a third image signal, in which
an optical path length from the mount surface to the third imaging element is longer than an optical path length from the mount surface to the second imaging element.

(8)

The medical imaging system according to (7), in which
the signal processing unit creates one all-pixel image using pixel values of Gr and Gb among pixel values of R, Gr, Gb, and B constituting the second image signal and the third image signal, and performs stationarity detection.

(9)

A medical imaging device including:
a first imaging element that receives light through a color filter and outputs a first image signal;
a second imaging element that receives light not through a color filter and outputs a second image signal;
an optical splitting system that splits incident light incident from a mount surface into light to be incident on the first imaging element and light to be incident on the second imaging element; and
a signal processing unit that performs depth-of-field extension processing to generate an extended-depth-of-field image obtained by extending a depth of field using the first image signal and the second image signal, in which
an optical path length from the mount surface to the first imaging element is shorter than an optical path length from the mount surface to the second imaging element.

(10)

An operation method for a medical imaging system, the method including:
receiving light obtained by splitting incident light incident from a mount surface and outputting a first image signal by a first imaging element;
receiving light split separately from the light and outputting a second image signal by a second imaging element; and
performing depth-of-field extension processing to generate an extended-depth-of-field image obtained by extending a depth of field using the first image signal and the second image signal, in which
the medical imaging system is configured such that an optical path length from the mount surface to the first imaging element is shorter than an optical path length from the mount surface to the second imaging element.

It should be noted that the embodiments of the present disclosure are not limited to the abovementioned embodiments, and various modifications can be made without departing from the gist of the present disclosure. In addition, the effects described in the present specification are merely illustrative and not restrictive, and may have additional effects.

REFERENCE SIGNS LIST

11 Medical imaging system
12 Medical imaging device
13 Signal processing device
20 Mount
21 Optical splitting system
22 Imaging module
31 First prism
32 Second prism
33 Half mirror
34 Third prism
35 Half mirror
41 Housing
42 Cover glass
43 Imaging element
44 Filter

The invention claimed is:

1. A medical imaging system, comprising:
a first imaging element that receives light through a color filter and outputs a first image signal;
a second imaging element that receives light not through the color filter and outputs a second image signal;
an optical splitting system that splits incident light incident from a mount surface into light to be incident on the first imaging element and light to be incident on the second imaging element; and
a signal processing unit that performs depth-of-field extension processing to generate an extended-depth-of-field image obtained by extending a depth of field using the first image signal and the second image signal, wherein
an optical path length from the mount surface to the first imaging element is shorter than an optical path length from the mount surface to the second imaging element.

2. The medical imaging system according to claim 1, wherein
the optical splitting system includes an optical element that reflects a part of light and transmits a part of light, and
the optical element has a transmittance set according to a difference in sensitivity between the first imaging element and the second imaging element.

3. The medical imaging system according to claim 1, wherein
the signal processing unit performs stationarity detection on the second image signal and performs development processing on the first image signal using a result of the stationarity detection.

4. The medical imaging system according to claim 3, wherein
the signal processing unit acquires a difference between adjacent pixels in at least one of a horizontal direction, a vertical direction, or an oblique direction, and performs the stationarity detection assuming that stationarity appears in a direction in which the difference between the adjacent pixels is minimized.

5. The medical imaging system according to claim 3, wherein
the signal processing unit calculates a difference in contrast between the first image signal and the second image signal and performs processing to reduce the difference in contrast.

6. The medical imaging system according to claim 3, wherein
the signal processing unit changes a parameter and a method of the stationarity detection on a basis of a mode selected by a user or a surgical situation obtained by image recognition.

7. The medical imaging system according to claim 1, further comprising
a third imaging element that receives light through the color filter and outputs a third image signal, wherein
an optical path length from the mount surface to the third imaging element is longer than the optical path length from the mount surface to the second imaging element.

8. The medical imaging system according to claim 7, wherein
the signal processing unit creates one all-pixel image using pixel values of Gr and Gb among pixel values of R, Gr, Gb, and B constituting the second image signal and the third image signal, and performs stationarity detection.

9. A medical imaging device comprising:
a first imaging element that receives light through a color filter and outputs a first image signal;
a second imaging element that receives light not through the color filter and outputs a second image signal;
an optical splitting system that splits incident light incident from a mount surface into light to be incident on the first imaging element and light to be incident on the second imaging element; and
a signal processing unit that performs depth-of-field extension processing to generate an extended-depth-of-field image obtained by extending a depth of field using the first image signal and the second image signal, wherein
an optical path length from the mount surface to the first imaging element is shorter than an optical path length from the mount surface to the second imaging element.

10. An operation method for a medical imaging system, the method comprising:
receiving light obtained by splitting incident light incident from a mount surface and outputting a first image signal by a first imaging element;
receiving light split separately from the light and outputting a second image signal by a second imaging element; and
performing depth-of-field extension processing to generate an extended-depth-of-field image obtained by extending a depth of field using the first image signal and the second image signal, wherein
the medical imaging system is configured such that an optical path length from the mount surface to the first imaging element is shorter than an optical path length from the mount surface to the second imaging element.

* * * * *